(12) United States Patent
Baloch et al.

(10) Patent No.: US 8,332,061 B2
(45) Date of Patent: Dec. 11, 2012

(54) FEATURE DRIVEN RULE-BASED FRAMEWORK FOR AUTOMATION OF MODELING WORKFLOWS IN DIGITAL MANUFACTURING

(75) Inventors: Sajjad Baloch, Monmouth Junction, NJ (US); Konrad Sickel, Nuremberg (DE); Vojtech Bubnik, Plainsboro, NJ (US); Rupen Melkisetoglu, Princeton, NJ (US); Hui Xie, Plainsboro, NJ (US); Sergei Azernikov, Plainsboro, NJ (US); Andreas Reh, Nürnberg (DE); Artem Boltyenkov, Nürnberg (DE); Fred McBagonluri, East Windsor, NJ (US); Tong Fang, Morganville, NJ (US)

(73) Assignees: Siemens Audiologische Technik GmbH, Erlangen (DE); Siemens Hearing Instruments, Inc., Piscataway, NJ (US)

( * ) Notice: Subject to any disclaimer, the term of this patent is extended or adjusted under 35 U.S.C. 154(b) by 680 days.

(21) Appl. No.: 12/573,171

(22) Filed: Oct. 5, 2009

(65) Prior Publication Data
US 2010/0094446 A1    Apr. 15, 2010

Related U.S. Application Data

(60) Provisional application No. 61/104,321, filed on Oct. 10, 2008.

(51) Int. Cl.
*G06F 19/00* (2011.01)

(52) U.S. Cl. ............................. 700/98; 700/182; 706/47
(58) Field of Classification Search ................... 700/98, 700/182; 706/47
See application file for complete search history.

(56) References Cited

U.S. PATENT DOCUMENTS

| 2004/0101179 A1* | 5/2004 | Suryanarayanan et al. .. 382/128 |
| 2006/0269140 A1* | 11/2006 | Ramsay et al. ............... 382/191 |
| 2007/0189564 A1 | 8/2007 | Bindner |

FOREIGN PATENT DOCUMENTS
EP         1939776 A2    7/2008

* cited by examiner

*Primary Examiner* — Sean Shechtman (57) ABSTRACT

A method for designing a prosthetic device includes acquiring a three-dimensional image of an anatomical surface. A rules script for automatically performing a plurality of image processing rules using a script interpreter is executed. For each particular rule of the plurality of rules, one or more anatomical features that are relevant to the particular rule using a surface shaping engine are determined, the one or more determined anatomical features are automatically segmented from the acquired three-dimensional image using a feature detector, and the particular image processing rule is performed on the acquired three-dimensional image based on the automatically segmented anatomical features using a CAD tool. A prosthetic device design is produced based on the three-dimensional image upon which the rules of the plurality of image processing rules have been performed.

20 Claims, 5 Drawing Sheets

```
// Move helix peak down by HelixShift
ShiftedHelixPeak = HelixPeak - HelixShift * BottomCutFlarePlane.Normal
// Move tragus
ShiftedTragus = Tragus - TragusShift * BottomCutFlarePlane.Normal
// Move down by ConchaShift
ShiftedCCIPoint = CrusConchaIntersection - ConchaShift * BottomCutFlarePlane.Normal
SanityCheck(ShiftedHelixPeak, ShiftedTragus, ShiftedCCIPoint)
BottomPlane = Plane(ShiftedHelixPeak, ShiftedTragus, ShiftedCCIPoint)
if Below(BottomPlane, Tip) then
BottomPlane = - BottomPlane
end
```

Sample section of script illustrating rules for describing the placement of a hearing aid vent within an ear surface in accordance with exemplary embodiments of the present invention

Fig. 4

```
if IsNotchSideVent then
      VentTop = InterTragalNotchTop
      VentDirection = CrusRidgeTop - InterTragalNotchTop
      VentBottom = InterTragalNotchBottom
else
      VentTop = CrusRidgeTop
      VentDirection = InterTragalNotchTop - CrusRidgeTop
      VentBottom = CrusRidgeBottom
end
VentOffset = VentWallThickness + VentDiameter / 2
Normalize(VentDirection)
VentTop = VentTop + VentDirection * VentOffset
PlaceVent(VentTop, TipPlane.Normal, VentBottom, BottomPlane.Normal)
```

Sample operation of vent placement CAD tool in accordance with exemplary embodiments of the present invention

Fig. 5

FEATURE DRIVEN RULE-BASED FRAMEWORK FOR AUTOMATION OF MODELING WORKFLOWS IN DIGITAL MANUFACTURING

CROSS-REFERENCE TO RELATED APPLICATION

The present application is based on provisional application Ser. No. 61/104,321, filed Oct. 10, 2008 the entire contents of which are herein incorporated by reference.

BACKGROUND OF THE INVENTION

1. Technical Field

The present disclosure relates to digital shape modeling and, more specifically, to feature driven rule-based framework for automatic modeling of organic shapes in digital manufacturing.

2. Discussion of Related Art

Digital shape modeling is the process by which the shape of a device to be manufactured is designed with the assistance of computer aided design (CAD) software. After the desired shape is modeled in CAD software, the model file may be used in fabrication to produce a device with the desired shape. The use of digital shape modeling is widespread, however, when used for the modeling of organic shapes, such as in the field of medical prostheses, the complexity, irregularity and uncertainty of shapes can pose particular problems for digital shape modeling. One important example is the field of custom hearing aid manufacture.

A hearing aid is an electroacoustic device for the amplification of sound. Modern hearing aids may be worn either partially or fully within the ear canal. Examples of such hearing aids include in the canal (ITC), mini canal (MIC), and completely in the canal (CIC) aids. For these types of hearing aids, the entire hearing aid is designed to fit securely in the wearer's ear. To achieve this secure fit, the hearing aid is incorporated into an outer shell that is custom fitted to the shape of the wearer's ear canal.

Custom fitting of the hearing aid shell is accomplished by first taking an impression of the wearer's ear canal. This may be achieved by applying hardening foam or other molding substance into the ear of the wearer. Once removed and allowed to harden, the three-dimensional shape of the mold may be digitally scanned and imported into CAD software. Technicians may then perform various modifications and transformations to the three-dimensional image to convert the image of the wearer's ear into a model for fabricating the shell of a hearing aid. These image processing steps may be labor intensive, tedious and prone to error. These factors may then add to the cost and time required to produce a suitable hearing aid.

SUMMARY

A method for designing a prosthetic device includes acquiring a three-dimensional image of an anatomy, which may be, for example, a solid image or a surface represented in three-dimensions or any similar representation from which the actual anatomical surface may be recovered (such as its implicit representation). A rules script for automatically performing a plurality of rules for processing an image, for example, a surface image or a solid image, using a script interpreter is executed. For each particular rule of the plurality of rules, one or more anatomical features that are relevant to the particular rule using a surface shaping engine are determined, the one or more determined anatomical features are automatically segmented from and/or detected on the acquired three-dimensional image using a feature detector, and the particular image processing rule is performed on the acquired three-dimensional image based on the automatically segmented and/or detected anatomical features using a CAD tool. The particular image processing rule may be performed, for example, by interpreting an abstract rule from a script to provide a precise surface modification operation. It may then be the precise surface modification operation that is performed on the surface. A prosthetic device design is produced based on the three-dimensional image upon which the rules of the plurality of image processing rules has been performed.

The anatomical surface may be an inner surface of an ear. The prosthetic device design may be a design for the outer shell of a hearing aid. The three-dimensional image of the inner surface of the ear may be acquired by digitally scanning a mold impression of the inner surface of the ear.

The rules script may be constructed using a custom scripting language to encapsulate existing work instructions for image processing into a computer-readable form.

The rules script may include a decision tree for the performance of the plurality of rules and the script interpreter uses this decision tree to determine which of the plurality of rules are to be performed and in what order.

The CAD tool need not require human interaction to perform the particular image processing rule on the acquired three-dimensional image. Alternatively, the CAD tool may receive human interaction in performing the particular image processing rule on the acquired three-dimensional image. For example, exemplary embodiments of the present invention may be implemented in the form of a guide or wizard in a semi-automatic setting. Here, the result of each step may be displayed to a user. The user may then have the opportunity to accept, modify or reject automatic processing steps, as desired. The user may also be able to execute other image processing steps and/or make arbitrary modifications. The user may also be able to define custom operations and/or skip steps altogether.

The anatomical surface may be an outer surface of a limb or bodily appendage. The prosthetic device design may be a design for the outer shell of an orthopedic prosthetic. Alternatively, the anatomical surface may be a bottom surface of a foot and the prosthetic device design may be a design for an orthotic device. Alternatively, the anatomical surface may be a surface of a mouth and the prosthetic device design may be a design for an orthodontic device or a dental prosthesis.

A system for designing a prosthetic device includes an image receiver for receiving a three-dimensional image of an anatomical surface, a script interpreter for executing a rules script for automatically performing a plurality of image processing rules, a surface shaping engine for determining one or more anatomical features that are relevant to a particular rule of the plurality of image processing rules, a feature detector for automatically segmenting and/or detecting the one or more determined anatomical features from the acquired three-dimensional image, and a CAD tool for performing the particular image processing rule on the acquired three-dimensional image based on the automatically segmented and/or detected anatomical features.

The rules script may include work instructions for image processing programmed into a computer-readable form using a custom scripting language. The rules script may be part of a knowledge base that is accessed by the script interpreter.

The script interpreter, the surface shaping engine, the feature detector and the CAD tool may be part of a smart shape modeler.

The CAD tool may include a plurality of image processing components for performing diverse image processing rules.

A computer system includes a processor and a program storage device readable by the computer system, embodying a program of instructions executable by the processor to perform method steps for designing a prosthetic device. The method includes acquiring a three-dimensional image of an anatomical surface, for example, using a 3D laser scanner. A rules script for automatically performing a plurality of image processing rules is executed using a script interpreter. For each particular rule of the plurality of rules one or more anatomical features that are relevant to the particular rule are determined using a surface shaping engine, the one or more determined anatomical features are automatically segmented from and/or detected on the acquired three-dimensional image using a feature detector, and the particular image processing rule is performed on the acquired three-dimensional image based on the automatically segmented anatomical features using a CAD tool. A prosthetic device design is produced based on the three-dimensional image upon which the rules of the plurality of image processing rules has been performed.

The anatomical surface may be an inner surface of an ear and the prosthetic device design is a design for the outer shell of a hearing aid. The three-dimensional image of the inner surface of the ear may be acquired by digitally scanning a mold impression of the inner surface of the ear.

The rules script may be constructed using a custom scripting language to encapsulate existing work instructions for image processing into a computer-readable form.

The CAD tool need not require human interaction to perform the particular image processing rule on the acquired three-dimensional image.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention seek to provide a framework by which the processing of organic shapes may be automatically performed to fabricate hearing aids, implants or other prosthetic devices that conform to underlying anatomy.

As discussed above, traditionally, the processing of anatomical models involves a high degree of interaction by a technician with knowledge of CAD software and the relevant human anatomy. These technicians generally rely on sets of vaguely defined work instructions to carry out a sequence of surface modification operations using interactive CAD tools. Exemplary embodiments of the present invention seek to remove several steps of human interaction to provide an automated approach to prosthetic design that is less costly, quicker, less prone to human error, capable of demonstrating a high degree of reproducibility, and easy to redo with desired modifications. This may be accomplished, in part, by translating the work instructions and the expert knowledge into machine interpretable rules, which in conjunction with robustly identified canonical set of anatomical features determine surface shaping operations. These operations may then be performed sequentially to adapt a surface to a target shape.

The versatility of this approach may be achieved by utilizing a predefined workflow that is implemented, for example, using a scripting language, thereby yielding a high degree of automation that is flexible and is customizable via scriptable rules. Consequently, tedious manual intervention may be reduced and a higher degree of precision and reproducibility may be achieved.

Exemplary embodiments of the present invention are herein described in terms of application to the automatic modeling of three-dimensional shells in hearing aids, however, it is to be understood that the techniques discussed herein may be readily applied to modeling of other organic shapes including, but not limited to, implants and prosthetics.

When employing computer assisted modeling of organic shapes, such as for use in the digital manufacturing of hearing aids, the designed shell surface should be able to adequately hold essential functional components such as electronics in their proper location and orientation to provide proper functionality. Additionally, the shell surfaces should demonstrate a tolerable degree of conformity with the underlying anatomy. The latter is particularly important to ensure that the resulting hearing aid conveniently fits within the ear of the wearer with ease and comfort. Due to the high degree of biological variability in patient's ear canals and other organic structures, the design of such shapes has traditionally been carried out manually. Expert designers may start with a surface representation of the underlying anatomy as an anatomical template, which may be acquired through 3D laser or CT scans of either a mold of the organic structure or by direct acquisition. The template may then be modified by a sequence of manual operations, which are defined or vaguely described in application specific work instructions. To this end, the designers rely on certain biomarkers on a template to ensure the conformity between the anatomy and the resulting shape.

Particularly, in the case of hearing aid (HA) manufacturing, orthopedics, orthotics, and orthodontics, tedious amounts of manual involvement are generally required. In-the-ear HAs are generally custom made to ensure a comfortable fit to the ear(s) of a patient. A wide range of HA configurations exist to cater for various levels of hearing losses as well as different styles. HA designers, therefore, rely on their experience along with lengthy work instructions for carrying out surface modifications via interactive CAD tools.

The large degree of variation across individuals' ear canal shape has thus far been a major hurdle to the performance of automated modeling of digital hearing aid design. Exemplary embodiments of the present invention specifically address these limitations by automating the steps that are generally performed by CAD technicians using fully automatic tools.

Figure 1:
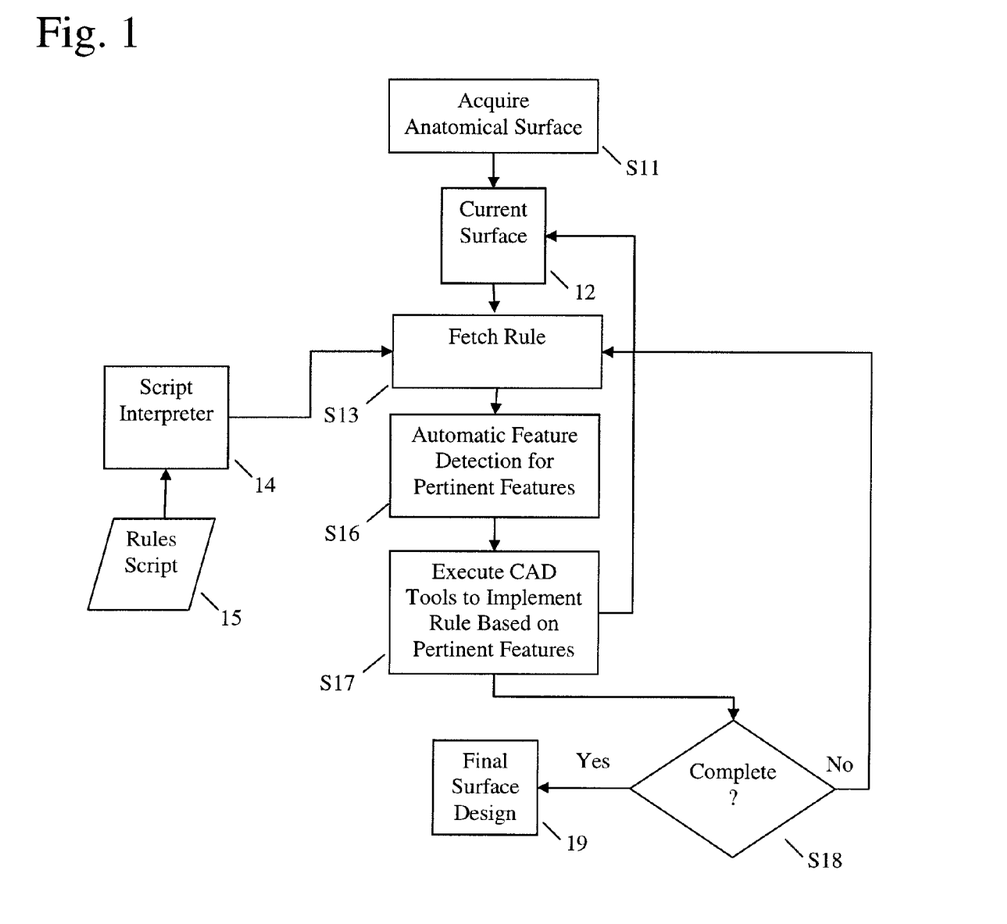
FIG. 1 is a flowchart illustrating a method for automatically modeling an organic shape according to an exemplary embodiment of the present invention.

FIG. 1 is a flowchart illustrating a method for automatically modeling an organic shape according to an exemplary embodiment of the present invention. First the anatomical surface may be acquired (Step S11). Acquisition of the anatomical surface may include retrieving the image data from a database or by digitization of a mold that has been cast of the patient's ear; however, other means for acquisition may be employed such as the performance of medical imaging. The acquired anatomical surface may then be considered the "current surface" 12 which is the surface that CAD processing tools are to be performed on. As CAD processing tools are applied to the current surface, the current surface may change form; however, the original acquired anatomical surface may also be retained.

Rules may then be fetched (Step S13). The rules may be retrieved by a script interpreter 14 from a rules script 15, both of which are descried in detail below. The rules represent the course of processing that is to be performed on the acquired anatomical surface to produce the final surface design 19. The rules may have been pre-programmed into the rules script 15, for example, based on existing sets of application-specific work instructions. The rules may represent a detailed decision tree and thus the script interpreter 14 may interpret the rules script 15 so that the appropriate rule may be fetched (Step S13). Each rule may make use of one or more anatomical landmarks within the anatomical surface. A rule may be, for example, to identify the plane of separation between the ear canal and the outer ear and to divide the current surface at that plane and discard the image information pertaining to the outer ear so that only the image data relating to the inner ear remains. As these rules may rely on identification of one or more pertinent anatomical landmarks, exemplary embodiments of the present invention may invoke a feature detection function for automatically segmenting the anatomical surface to identify one or more pertinent anatomical features (Step S16) that may be used to implement the fetched rule. As automatic segmentation and/or detection may be time consuming and resource intensive, exemplary embodiments of the present invention may limit automatic detection and/or segmentation to identifying only those anatomical features that are pertinent to the currently fetched rule; however, exemplary embodiments of the present invention may also perform a full segmentation at this point so that all anatomical features that may be used by the rules script 15 may be automatically identified during a single step.

The anatomical features that are automatically detected and/or segmented may be found within the originally acquired surface. However, anatomical features may also be found within the current surface, which may be the surface upon which the image processing steps have been applied to.

After the pertinent anatomical features have been identified (Step S16), CAD tools may be executed to implement the fetched rule based on the pertinent features (Step S17). To use the example described above, the step of automatic feature detection (Step S16) may include segmenting the ear canal from the outer ear and the step of executing the CAD tools to implement the rule based on the pertinent features (Step S17) may include dividing the anatomical surface at the plane of separation between the segmented outer ear and the ear canal and discarding image information pertaining to the outer ear.

It should be noted that the current surface image may be modified by the implementation of the rules by the CAD tools.

It may then be determined whether there are additional rules to implement or if the current surface has been finalized (Step S18). If the current surface has not been finalized (No, Step S18) then the next rule may be fetched (Step S13). If, however, the current surface has been finalized (Yes, Step S18) then the current surface 12 may be the final surface design 19. The final surface design may then be used in the fabrication of the hearing aid or other device.

As discussed above, the surface shaping steps are defined in the form of work instructions. By following these instructions a user performs interactively surface modification operations using key landmarks on a surface. Exemplary embodiments of the present invention, however, may simulate this process through a smart modeling framework. This framework may combine the information in the work instructions with the surface landmarks to express surface shaping operations in the form of a rules script. This framework for creating the rules script may have two major components, namely a knowledge base (KB), and a smart shape modeler (SSM).

Figure 2:
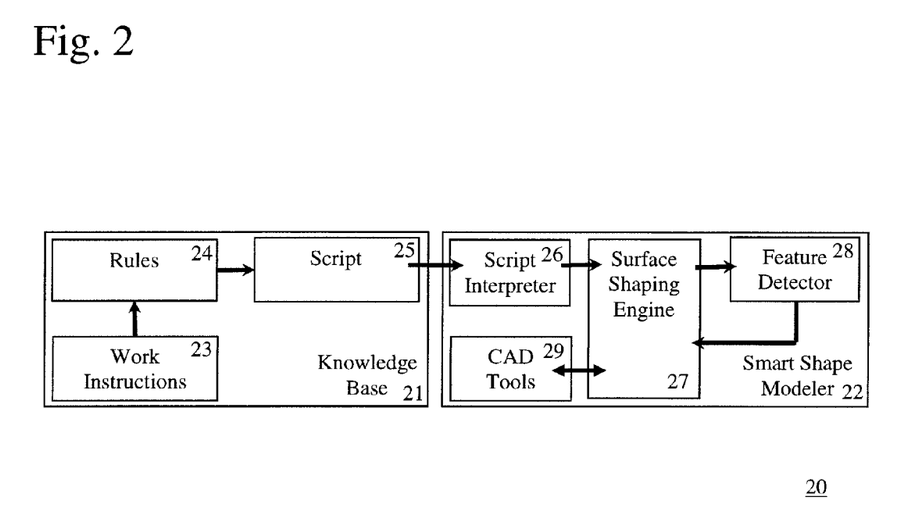
FIG. 2 is an illustration of a framework for developing feature driven rules according to an exemplary embodiment of the present invention.

FIG. 2 is an illustration of a framework 20 for developing feature driven rules according to an exemplary embodiment of the present invention. It is these feature driven rules that may be incorporated into the rules script discussed above. The first part of the framework 20 may be the knowledge base 21. The knowledge base 21 may digitally represent the workflow of the work instructions 23 in the form of a set of rules 24 derived from the work instructions 23. The rules 24 may be application specific and designed to ensure that they are consistent across all realizations of a particular class of surfaces. They may describe both how to perform various steps consistently, and which features to utilize in a particular step. A step, in turn, may consist of one or more surface modification operations and may combine features for carrying them out. For example, for cutting a surface, the knowledge base may specify a rule that defines where to perform a cut consistently for a wide range of surfaces of the same class. Accordingly, the corresponding rule should be able to compute the cutting plane, as well as the type of the cut. Although surfaces may exhibit variability, their class membership may ensure that some canonical set of features is always identifiable, and is sufficient enough to define such a plane.

The knowledge base 21 may implement the rules 24 as a script 25 in a scripting language. The scripting language, therefore, may allow for a flexible customization of the rules 24 for various shell classes and target shapes.

The second part of the framework may be the smart shape modeler 22. The smart shape modeler 22 may function to design a surface and/or shape via CAD tools 29, which are invoked automatically as directed by the knowledge base 21. To this end, a surface shaping engine 27 may interact with a script interpreter 26 to sequentially fetch rules from the digitized workflow. Each rule may be translated to an operation that is defined by particular features. Sequential execution of the script rules may be enabled by the script interpreter 26, which may parse the rules and maintain the state of the current rule in a digitized workflow. Once the surface shaping engine 27 identifies an operation(s) from the current rule and the associated features, it may query the feature detector 28 for the required features. Feature information may then be used to uniquely determine the operation to be performed in terms of its localization on the surface. An appropriate CAD tool 29 may then be invoked to perform the determined operation on the surface. For example, for local scooping or smoothing, the knowledge base 21 may inform the surface shaping engine 27 about the operation (for example, scooping or smoothing), the scooping or smoothing parameters (e.g., the amount of scooping/smoothing), and the identifier for the corresponding region of interest. Based on this identifier, the feature detector 28 may provide the surface shaping engine 27 with the area to be scooped or smoothed. The role of surface shaping engine 27 may be to route various commands in the script to various components.

The workflow automation framework including the knowledge base and the smart shape modeler may be used to execute the method described above with respect to FIG. 1. The script 25 of the knowledge base 21 may be used as the rules script 15 and may include a set of surface modification rules. The script interpreter 26 of the smart shape modeler 22 may be used as the script interpreter 14. Once a surface is specified, the surface shaping engine 27 may be used to fetch the rule in Step S13, reset the current state of the surface 12, and request that the script interpreter 14 and 26 to fetch the next rule (Step S13). From the rule, the set of required features may be identified (Step S16) along with the operation type and any associated parameters that may be required. The feature detector 28 may then be invoked to detect required features. These features may then be used to uniquely define the actual surface modification operation during the execution of the CAD tools 29 (Step S17). This information may lead to a selection of the desired tool with correct parameters, which may then be applied on the current surface. The process may be repeated until the script interpreter 26 is exhausted of all applicable rules 24 in the script 25. The current surface 12 may then be outputted as the final surface design 19. This modular framework may allow for the workflow modeler and the surface shaping engine to constitute a fully automated smart modeling system that is not specific to a particular application. One may readily switch between applications by modifying the scriptable rules and the associated feature set. In addition, for a given application, the smart modeling system may be highly configurable via scripting.

Since the rules may be executed sequentially, the underlying surface design software may be configured to allow either semiautomatic or fully automatic processing. When a semiautomatic processing is utilized, at each execution of CAD tools to implement rules based on pertinent features, a virtual surface may be generated by the CAD software. This surface may be displayed to the user as a preview image along with an option for changing CAD tool parameters. A user may thereby select the suggested result, make a modification, discard suggestion, and/or invoke an interactive mode. This may provide the user with flexibility to adapt the virtual surface before setting it as the current surface.

As described above, exemplary embodiments of the present invention may be applied to the modeling of hearing aid shells. Here, the acquired anatomical surface may be a digital scan of a mold of the wearer's ear. Ear impressions may first be acquired by an audiologist by inserting a mold through an injector deep in the ear canal. The mold may then be allowed to settle to the interior of the outer ear before taking out the impression and performing a three-dimensional digital scan on the mold. The resulting reconstructed surface represents the shape of the interior of the ear. Despite similarities in appearance, ear impressions are unique and exhibit large amount of biological variability across individuals. In addition, the missing data (holes or incomplete impressions) as well as formations of excess material may pose challenges to complete automation. For example, a ventilation tube (vent) may be placed along the ridge of a shell to minimize the space occupied in the hearing aid device. Incorrectly positioning the vent may cause collision with other internal hearing aid components and difficulties during the actual assembly process. Accordingly, optimal vent placement based on the automatically detected ridge area is crucial for the successful hearing aid design.

As described above, automatic feature detection may be performed by a feature detector of a smart shape modeler to automatically detect features that are pertinent to a particular rule being executed. The detected anatomical features may be considered canonical as they may capture comprehensive information about an ear for defining a set of generalized rules. They include point, plane, area, and curve features, which capture the bumps, bends, convexities, concavities, ridges, valleys and the intersections of ridges. Examples of anatomical features that may be detected include the canal tip, the center of the concha, the center of the crus, the helix peak, the center of the anti-helix, the crus-concha intersection, the center of the anti-tragus, the inter-tragal notch flare, the canal-concha intersection, the center low aperture, the crus area, the tragus area, the helix ridge area, the canal bulbous, the inter tragal notch, the crus-side canal ridge, the bottom cut flare plane, the aperture plane, the first bend plane, and the second bend plane.

As described above, the work instructions may be embodied as a set of rules that may be represented within a scripting language, for example, a scripting language that has been specifically designed for the task. Such a scripting language may make use of a context free grammar for realizing rules, for example, in the form of if-then-else statements, and generic as well as specialized functions. The script interpreter may then be implemented using code-generating tools such as Bison and Flex. The scripting language may support standard data types, in addition to geometric primitives such as points, planes, and matrices, which allow easy manipulation of surface meshes. This language may also support control structures, such as if then else blocks, and for, while, and repeat until loops. Specialized functions may also be used. Examples of specialized functions that may be used include interfaces to CAD tool APIs, Feature Detection Functions, and primitive surface manipulators.

A customized scripting language may be used to allow for simple handling of the scripts, and its easy integration with a CAD application. Accordingly, the CAD application may be kept flexible.

As described above, exemplary embodiments of the present invention may implement work instructions as a set of rules using a scripting language. As different hearing aid configurations may employ different combinations of features, these combinations may be expressed, in the scripting language, by the use of a decision tree including, for example, if-then-else statements in the script. Examples of rules may include "CutCanalAtSecondBend," "SmoothAtXYZAreaFeature," "CutShellWithPlaneDefinedByXYZPointFeatures," and "RoundShellAtXYZPlane."

Figure 3:
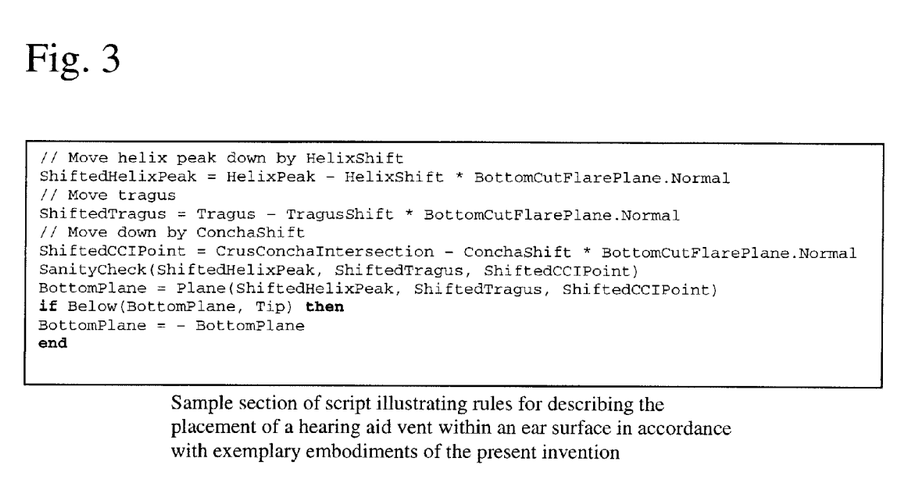
FIG. 3 is a sample section of script illustrating rules for describing the placement of a hearing aid vent within an ear surface in accordance with exemplary embodiments of the present invention.

Described herein, for the purposes of setting forth an example is a set of scripting rules for describing the placement of a hearing aid vent within an ear surface. FIG. 3 is a sample section of script illustrating rules for describing the placement of a hearing aid vent within an ear surface in accordance with exemplary embodiments of the present invention. As mentioned above, a vent is a tubular attachment to the canal of a hearing aid shell. In the simplest configuration, it may be placed along one of the canal ridges because of the acoustic principles and the size constraints. The side selection (notch-side ridge or crus-side ridge), the starting and ending points and the wall thickness of the vent may easily be specified through scripting rules. Since the vent runs from the tip of the canal to the bottom of a shell, the script should first define the tip and the bottom planes. The shell bottom may be defined in terms of three point features, namely helix peak, crus-concha intersection, and tragus.

Once these features are detected, a CAD cutting tool may be invoked on the surface to get rid of the excess material, for example, with the command:

CutSurface(BottomPlane, Tip)

Figure 4:
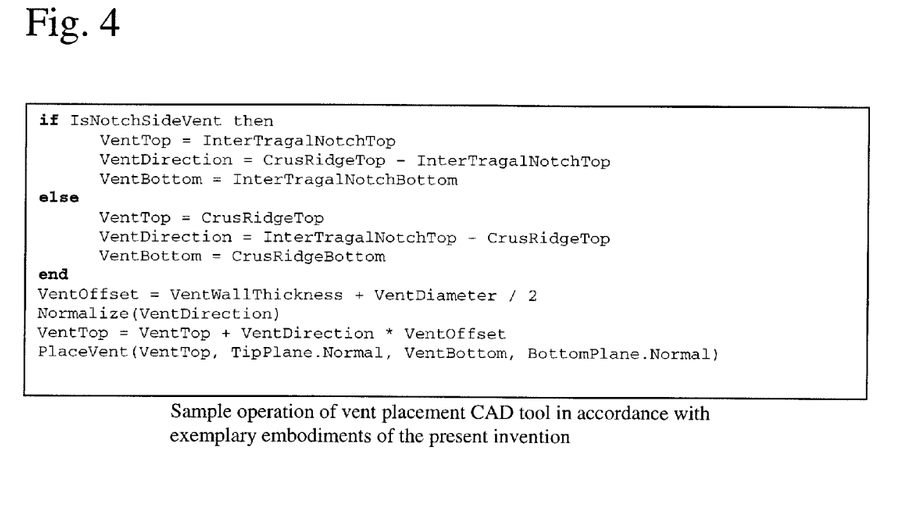
FIG. 4 is an example of a vent placement CAD tool according to an exemplary embodiment of the present invention.

The starting and ending points of the vent may be required for proper placement. Based on the vent side information, the vent may be placed along either the inter-tragal notch, or the crus-side ridge. The starting and ending points in either case are different, and may be found through features, such as the inter-tragal notch top and bottom points, or crusside ridge top and bottom points. The thickness of the vent wall may also be taken into account to ensure that the end points fall at the right place on the surface. FIG. 4 is an example of a vent placement CAD tool according to an exemplary embodiment of the present invention.

Accordingly, the knowledge base may contain these instructions in the form of a script, which are sufficient for a simple exemplary vent placement operation. When initialized with a given surface, the surface shaping engine may query the rule from the script interpreter, and executes each instruction. Features may then be detected on the fly, and the surface modification operation may be determined at the run-time.

Exemplary embodiments of the present invention may provide a framework for the automation of surface modeling workflows. Herein, human readable work instructions may be translated to machine interpretable rules. Consequently, interactive CAD operations may be performed automatically by automatic surface shaping operations dictated by the rules. The rules may be specified through a special scripting language and may be based on the features detected on a surface. As the rules may be diverse, approaches in accordance with exemplary embodiments of the present invention may be flexible and accordingly, various unique organic structures may be modeled in digital manufacturing.

The modular nature of this framework allows for general applicability to a wide range of applications, for example, the modeling of hearing aids, dentures, braces, orthotic devices, and orthopedic joint replacements. Accordingly, modeling may be automatic or semiautomatic and may be performed relatively quickly and inexpensively. Multiple orders may even be batched.

Figure 5:
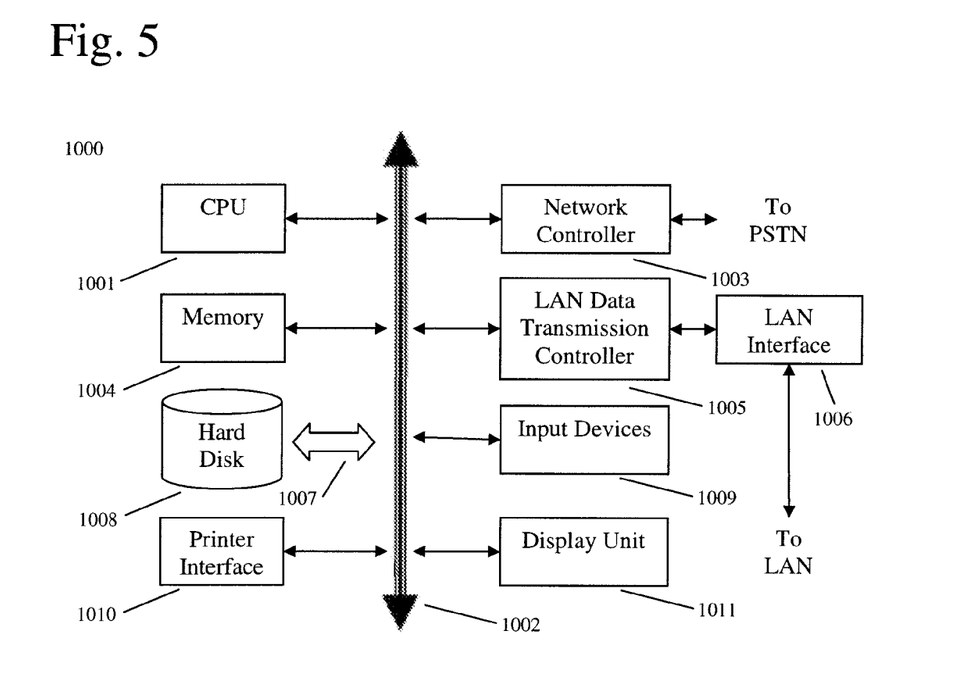
FIG. 5 shows an example of a computer system capable of implementing the method and apparatus according to embodiments of the present disclosure.

FIG. 5 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002; and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for designing a prosthetic device, comprising:
   acquiring a three-dimensional image of an anatomical surface;
   executing a rules script for automatically performing a plurality of image processing rules using a script interpreter;
   for each particular rule of the plurality of rules:
     determining one or more anatomical features that are relevant to the particular rule using a surface shaping engine,
     automatically segmenting or detecting the one or more determined anatomical features from the acquired three-dimensional image using a feature detector, and
     performing the particular image processing rule on the acquired three-dimensional image based on the automatically segmented or detected anatomical features using a CAD tool; and
   producing a prosthetic device design based on the three-dimensional image upon which the rules of the plurality of image processing rules has been performed.

2. The method of claim 1, wherein the step of performing the particular image processing rule includes:
   automatically determining a concrete surface modification operation based on the particular image processing rule, combined with the one or more automatically segmented or detected anatomical features; and
   performing the particular surface modification operation on the acquired three-dimensional image using the CAD tool.

3. The method of claim 1, wherein the three-dimensional image is a solid image, a surface represented in three-dimensions, or any representation from which an actual anatomical surface can be extracted; and the plurality of image processing rules includes rules for processing a solid image or a surface representation in three-dimensions.

4. The method of claim 1, wherein the anatomical surface is an inner surface of an ear and the prosthetic device design is a design for the outer shell of a hearing aid.

5. The method of claim 4, wherein the three-dimensional image of the inner surface of the ear is acquired by digitally scanning a mold impression of the inner surface of the ear.

6. The method of claim 1, wherein the rules script is constructed using a custom scripting language to encapsulate existing work instructions for image processing into a computer-readable form.

7. The method of claim 1, wherein the rules script includes a decision tree for the performance of the plurality of rules and the script interpreter uses this decision tree to determine which of the plurality of rules are to be performed and in what order.

8. The method of claim 1, wherein the CAD tool does not require human interaction to perform the particular image processing rule on the acquired three-dimensional image.

9. The method of claim 1, wherein the CAD tool receives human interaction in performing the particular image processing rule on the acquired three-dimensional image.

10. The method of claim 1, wherein the anatomical surface is an outer surface of a limb or bodily appendage and the prosthetic device design is a design for the outer shell of an orthopedic prosthetic.

11. The method of claim 1, wherein the anatomical surface is a bottom surface of a foot and the prosthetic device design is a design for an orthotic device.

12. The method of claim 1, wherein the anatomical surface is a surface of a mouth and the prosthetic device design is a design for an orthodontic device or a dental prosthesis.

13. A system for designing a prosthetic device, comprising:
an image receiver for receiving a three-dimensional image of an anatomical surface;
a script interpreter for executing a rules script for automatically performing a plurality of image processing rules;
a surface shaping engine for determining one or more anatomical features that are relevant to a particular rule of the plurality of image processing rules;
a feature detector for automatically segmenting or detecting the one or more determined anatomical features from the acquired three-dimensional image; and
a CAD tool for performing the particular image processing rule on the acquired three-dimensional image based on the automatically segmented or detected anatomical features; and
a computer producing a prosthetic device design based on the three-dimensional image upon which the rules of the plurality of image processing rules has been performed.

14. The system of claim 13, wherein the three-dimensional image is a solid image, a surface represented in three-dimensions, or a representation from which the actual anatomical surface can be extracted; and the plurality of image processing rules includes rules for processing a solid image or a three-dimensional surface representation.

15. The system of claim 13 wherein the rules script includes work instructions for image processing programmed into a computer-readable form using a custom scripting language.

16. The system of claim 13, wherein the rules script is part of a knowledge base that is accessed by the script interpreter.

17. The system of claim 13, wherein the script interpreter, the surface shaping engine, the feature detector and the CAD tool are part of a smart shape modeler.

18. The system of claim 13, wherein the CAD tool includes a plurality of image processing components for performing diverse image processing rules.

19. A computer system comprising:
a processor; and
a program storage device readable by the computer system, embodying a program of instructions executable by the processor to perform method steps for designing a prosthetic device, the method comprising:
acquiring a three-dimensional image of an anatomical surface;
executing a rules script for automatically performing a plurality of image processing rules using a script interpreter;
for each particular rule of the plurality of rules:
determining one or more anatomical features that are relevant to the particular rule using a surface shaping engine,
automatically segmenting or detecting the one or more determined anatomical features from the acquired three-dimensional image using a feature detector, and
performing the particular image processing rule on the acquired three-dimensional image based on the automatically segmented or detected anatomical features using a CAD tool; and
producing a prosthetic device design based on the three-dimensional image upon which the rules of the plurality of image processing rules has been performed.

20. The computer system of claim 19, wherein the three-dimensional image is a solid image, a surface represented in three-dimensions, or a representation from which an actual anatomical surface can be extracted; and the plurality of image processing rules includes rules for processing a solid image or a three-dimensional surface representation.

* * * * *